(12) United States Patent
Timken et al.

(10) Patent No.: US 10,683,460 B2
(45) Date of Patent: Jun. 16, 2020

(54) ETHYLENE OLIGOMERIZATION PROCESS FOR MAKING HYDROCARBON LIQUIDS

(71) Applicants: Hye-Kyung Cho Timken, Albany, CA (US); Bong-Kyu Chang, Novato, CA (US); Curtis Bay Campbell, Hercules, CA (US); Andrew Michael Thomas, Albany, CA (US); Mark Anthony Fernandez, Fairfield, CA (US); Madeleine Sessions, San Francisco, CA (US)

(72) Inventors: Hye-Kyung Cho Timken, Albany, CA (US); Bong-Kyu Chang, Novato, CA (US); Curtis Bay Campbell, Hercules, CA (US); Andrew Michael Thomas, Albany, CA (US); Mark Anthony Fernandez, Fairfield, CA (US); Madeleine Sessions, San Francisco, CA (US)

(73) Assignees: Chevron Oronite Company LLC, San Ramon, CA (US); Chevron U.S.A. Inc., San Ramon, CA (US)

( * ) Notice: Subject to any disclaimer, the term of this patent is extended or adjusted under 35 U.S.C. 154(b) by 72 days.

(21) Appl. No.: 15/910,957

(22) Filed: Mar. 2, 2018

(65) Prior Publication Data
US 2018/0251691 A1 Sep. 6, 2018

Related U.S. Application Data

(62) Division of application No. 14/674,918, filed on Mar. 31, 2015, now Pat. No. 9,938,473.

(51) Int. Cl.
*C10G 50/00* (2006.01)
*C10L 1/04* (2006.01)
(Continued)

(52) U.S. Cl.
CPC ............... *C10G 50/00* (2013.01); *C07C 2/22* (2013.01); *C10G 57/02* (2013.01); *C10L 1/04* (2013.01); *C10L 1/08* (2013.01); *C10M 101/02* (2013.01); *B01J 31/0284* (2013.01); *B01J 31/0298* (2013.01); *B01J 2231/20* (2013.01);
(Continued)

(58) Field of Classification Search
None
See application file for complete search history.

(56) References Cited

U.S. PATENT DOCUMENTS 5,071,576 A * 12/1991 Vernet .................. C10M 159/24
508/398
5,112,506 A * 5/1992 Marsh .................. C10M 159/24
508/391

(Continued)

FOREIGN PATENT DOCUMENTS

WO 2012/087380 A1 6/2012

OTHER PUBLICATIONS

Stenzel et al., "Oligomerization of olefins in a chloroaluminate ionic liquid," J. Mol. Catal. A. Chem. 192(1-2):217-222 2003).

*Primary Examiner* — Tam M Nguyen
(74) *Attorney, Agent, or Firm* — Jones Day

(57) ABSTRACT

Provided herein are processes for ethylene oligomerization in the presence of an ionic liquid catalyst and a co-catalyst to produce a hydrocarbon product comprising $C_{10}$-$C_{55}$ oligomers.

6 Claims, 3 Drawing Sheets

(51) Int. Cl.
*C10L 1/08* (2006.01)
*C10M 101/02* (2006.01)
*C07C 2/22* (2006.01)
*C10G 57/02* (2006.01)
*B01J 31/02* (2006.01)

(52) U.S. Cl.
CPC .... *C07C 2527/11* (2013.01); *C07C 2527/125* (2013.01); *C10G 2300/1022* (2013.01); *C10G 2300/1092* (2013.01); *C10G 2400/04* (2013.01); *C10G 2400/08* (2013.01); *C10G 2400/10* (2013.01); *C10L 2200/043* (2013.01); *C10L 2200/0446* (2013.01); *C10L 2270/026* (2013.01); *C10L 2270/04* (2013.01); *C10L 2290/543* (2013.01); *Y02P 20/52* (2015.11)

(56) References Cited

U.S. PATENT DOCUMENTS

| | | | |
|---|---|---|---|
| 5,463,158 A | | 10/1995 | Goledzinowski et al. |
| 6,008,164 A | * | 12/1999 | Aldrich .................. C10G 2/30 208/18 |
| 7,432,408 B2 | | 10/2008 | Timken et al. |
| 7,495,144 B2 | | 2/2009 | Elomari |
| 7,531,707 B2 | | 5/2009 | Harris et al. |
| 7,674,739 B2 | | 3/2010 | Elomari et al. |
| 7,732,364 B2 | | 6/2010 | Chang et al. |
| 7,955,495 B2 | | 6/2011 | Hommeltoft et al. |
| 8,070,939 B2 | | 12/2011 | Hommeltoft et al. |
| 8,124,821 B2 | | 2/2012 | Elomari et al. |
| 8,222,471 B2 | | 7/2012 | Elomari et al. |
| 8,436,221 B2 | | 5/2013 | Hommeltoft et al. |
| 8,471,086 B2 | | 6/2013 | Hommeltoft |
| 8,524,968 B2 | | 9/2013 | Elomari et al. |
| 8,586,812 B2 | | 11/2013 | Timken et al. |
| 2007/0021560 A1 | * | 1/2007 | Tse .......................... C08L 23/02 525/88 |
| 2007/0142691 A1 | | 6/2007 | Elomari et al. |
| 2008/0317990 A1 | * | 12/2008 | Runyan .................. B29C 71/04 428/36.9 |
| 2009/0029889 A1 | * | 1/2009 | Poirier ................. C10M 129/50 508/479 |
| 2010/0025292 A1 | * | 2/2010 | Hommeltoft ........ C10G 57/005 208/95 |
| 2010/0025298 A1 | | 2/2010 | Hommeltoft et al. |
| 2011/0319693 A1 | * | 12/2011 | Hommeltoft ............. C07C 2/60 585/711 |
| 2016/0289574 A1 | * | 10/2016 | Timken ................. C10G 50/00 |

* cited by examiner

ETHYLENE OLIGOMERIZATION PROCESS FOR MAKING HYDROCARBON LIQUIDS

RELATED APPLICATIONS

This application is a divisional under 35 U.S.C. § 121, of U.S. application Ser. No. 14/674,918, filed Mar. 31, 2015, now U.S. Pat. No. 9,938,473, the disclosure of which is incorporated herein by reference in its entirety.

FIELD OF THE INVENTION

Provided herein are processes for oligomerization of ethylene in presence of a liquid ionic catalyst to obtain a hydrocarbon product. The hydrocarbon product is useful, for example, in jet fuel, diesel and lubricating oil.

BACKGROUND OF THE INVENTION

A variety of oligomerization catalysts, both homogeneous and heterogeneous, have been utilized to oligomerize ethylene into olefinic products or alkenes of higher molecular weight. Linear Alpha Olefins (LAO) or Normal Alpha Olefins (NAO) in a $C_4$-$C_{28}$ hydrocarbon range are commercially manufactured by using various ethylene oligomerization processes including the Shell Oil Company SHOP process (using a molecular active Ni catalyst) or Ineos process (Ethyl Corporation) or Gulf process (ChevronPhillips Company) or Sabic Linde α-Sablin process or IFP-Axens AlphaSelect process, where alky aluminum catalysts (typically Ziegler Natta type systems) are used to produce even number carbon alpha olefins with a statistical bell curve shape of carbon number distribution (Schulz-Flory distribution).

Ethylene dimerization and trimerization processes are also known. For example, the IFP-Axens Alphabutol Process and Dimersol E technologies employ titanium-containing catalysts for dimerization. The ethylene trimerization process to produce 1-hexene using a chrome-containing catalyst was commercialized by the ChevronPhillips Company.

Ethylene feeds for these processes are produced by an on-purpose ethylene producing plant where pure ethylene with 99.99%+ purity is isolated using very expensive, state-of-the art distillation columns. Ethylene dimerization, trimerization, and oligomerization processes typically use only pure ethylene for their feeds since the dimerization, trimerization, and oligomerization catalysts are extremely susceptible to poisoning by impurities. Even a small amount of poisons such as sulfur, nitrogen containing compounds, oxygenates, dienes, and trace metals can deactivate the catalysts.

The petrochemical and petroleum industry produces many hydrocarbon streams containing ethylene. However, the separation of pure ethylene from these process streams and/or separation of impurities for catalytic operations are often not undertaken nor economical (due to the added processing unit operations) and the streams are commonly used as lower value fuels to generate steam.

Conventional catalysts such as zeolite or mineral acid cannot oligomerize ethylene to make jet and diesel range hydrocarbon with acceptable conversion and selectivity. Use of an ionic liquid catalyst for alkylation of ethylene with isoparaffins was described in, for example, U.S. Pat. No. 7,432,408 and US Patent Application No. 2011/0319693 where ethylene was reacted with isopentane or isobutane to make alkylate gasoline products, predominantly $C_7$ or $C_6$ hydrocarbon.

There is a need for a process that can be applied to a mixed hydrocarbon stream containing ethylene to oligomerize ethylene into a high value hydrocarbon product using ionic liquid catalysts to obtain jet and diesel fuel and satisfy the increasing market demand for hydrocarbons in the jet and diesel fuel range. Furthermore, there is a need for an ethylene oligomerization process in which high ethylene conversion and good diesel selectivity are obtained from a feed stream containing low-purity ethylene.

SUMMARY OF THE INVENTION

In certain embodiments, provided herein is an efficient ethylene oligomerization process to convert ethylene to higher molecular weight hydrocarbon products of commercial importance, for example, the production of jet fuels, diesel fuels, and lubricating oil blend stocks.

In certain embodiments, provided herein is a process for ethylene oligomerization in the presence of an ionic liquid catalyst and a co-catalyst to produce a hydrocarbon product comprising hydrocarbons predominantly boiling in jet, diesel and base oil product range.

In one embodiment, provided herein is a hydrocarbon product prepared by the processes disclosed herein. In one embodiment, the hydrocarbon yield is greater than 30% by weight of the ethylene feed. In one embodiment, the hydrocarbon product has greater than 45 wt % of the hydrocarbon oligomer boiling in 250° F. (121° C.)-700° F. (371° C.). In certain embodiments, the hydrocarbon product comprises $C_{10}$-$C_{55}$ and the average carbon number is in the range of $C_{15}$ to $C_{40}$. In certain embodiments, the hydrocarbon product has olefinic hydrogen content less than 2 mol % of the total hydrogen measured by $^1$H NMR.

The hydrocarbon product produced by the processes provided herein has use in, for example, jet fuels, diesel fuels, and lubricating oil blend stocks. In certain embodiments, the proportion of the co-catalyst and ethylene in the oligomerization process provided herein can be adjusted to shift the product boiling range to obtain the hydrocarbon fractions suitable for jet fuels, diesel fuels or lubricating oil blend stocks. This process provided herein can be used to oligomerize a pure ethylene feed or dilute gas stream comprising an olefin that is predominately ethylene containing olefins. By converting ethylene to jet fuel and diesel blending stock, a significant value uplifting is achieved.

DETAILED DESCRIPTION

Figure 1:
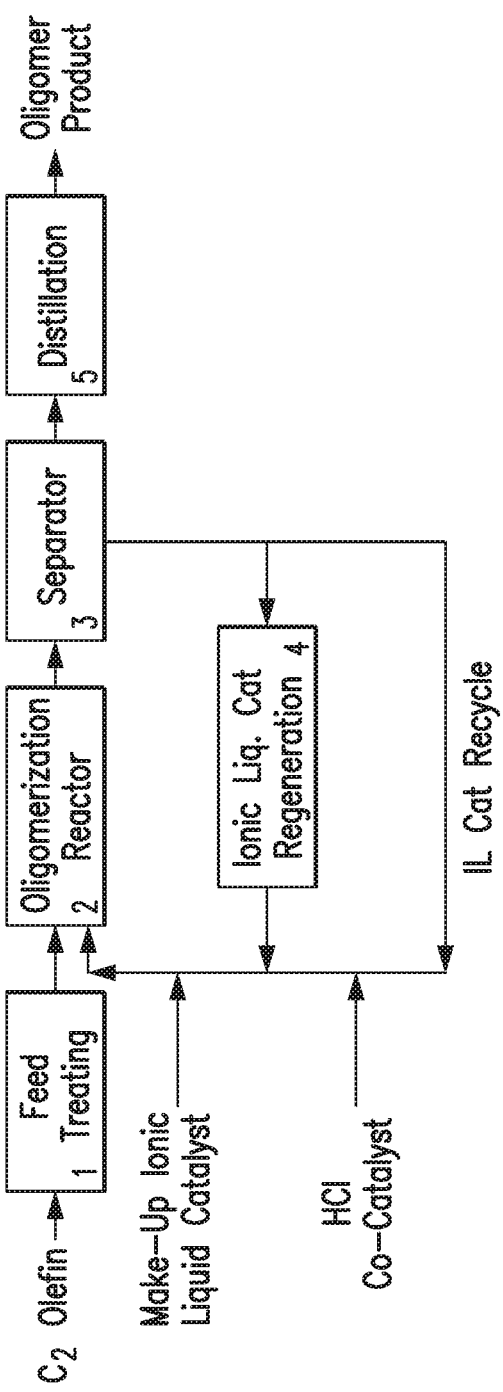
FIG. 1 provides a flow chart illustrating an exemplary oligomerization process.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed.

In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

Any term, abbreviation or shorthand not defined is understood to have the ordinary meaning used by a skilled artisan contemporaneous with the submission of this application.

As used herein, the term "$C_x$ hydrocarbon" indicates hydrocarbon molecules having the number of carbon atoms represented by the subscript "x". The term "$C_x+$ hydrocarbons" indicates hydrocarbon molecules having the number of carbon atoms represented by the subscript "x" or greater. For example, "$C_{20}+$ hydrocarbons" includes $C_{20}$, $C_{21}$ and higher carbon number hydrocarbons. Similarly "$C_{20}-$ hydrocarbons" indicates those molecules having the number of carbon atoms represented by the subscript "x" or fewer.

As used herein, "feed" or "feed stream" refers to an ethylene feed or a gas stream comprising ethylene.

As used herein, the term "branching index" or "BI" is defined as the % ratio of integral values of the methyl group ($CH_3$) protons compared to the sum of the methylene (—$CH_2$—), methinyl (—CH—) and methyl (—$CH_3$) group protons. The branching index is determined using Equation 1 as described in Example 7.

As used herein, the term "range of carbon number" or "carbon number distribution" is defined as the lowest carbon number with at least 2% relative intensity to the highest carbon number with at least 2% relative intensity in a spectrum obtained by Field Ionization Mass Spectrometer (FIMS).

As used herein, the term "average carbon number" is defined as the molecular ion at the center of the distribution range in a spectrum obtained by Field Ionization Mass Spectrometer (FIMS).

As used herein, a hydrocarbon fraction for jet fuel/ kerosene refers to a fraction having boiling points in the range from 250° F.-500° F. (121-260° C.). A hydrocarbon fraction for diesel fuel refers to a fraction having boiling points in the range from 400° F.-700° F. (204-371° C.). A hydrocarbon fraction for lubricating base stock refers to a fraction having boiling points greater than 650° F. (343° C.), in certain embodiments, greater than 700° F. (371° C.). A hydrocarbon fraction for jet, kerosene and diesel fuel refers to a fraction having boiling points in the range from 250° F.-700° F. (121-371° C.).

In certain embodiments, provided herein is a process for ethylene oligomerization comprising contacting a feed stream with an ionic liquid catalyst and a co-catalyst in an oligomerization reactor under olefin oligomerization conditions to produce a hydrocarbon product. The product provided herein uses a feed stream containing an olefin that is predominately ethylene, which is selectively oligomerized to make $C_{10}$-$C_{55}$ hydrocarbon product. In this regard, the olefin feed comprises a major amount of ethylene based on the total mole charge of the olefins in the olefin feed, thus the molar ratio of higher carbon number olefins to ethylene can be 0.5 or less, 0.3 or less, 0.1 or less, or 0.05 or less.

Unlike the ethylene alkylation process disclosed in US Patent Publication No. 2011/0319693, the process provided herein does not require deliberate feeding of isoparaffin and recycling of unreacted, excess isoparaffin. In certain embodiments, the isoparaffin reaction product is incorporated in the hydrocarbon product and does not require further separation.

The product obtained in the process comprises $C_{10}$-$C_{55}$ oligomers. In certain embodiments, the $C_{10}$-$C_{55}$ oligomer product comprises oligomer fractions having boiling points in the range from about 200° F. (93° C.) to about 1000° F. (538° C.). The products obtained in the processes provided herein are used in jet fuel, kerosene, diesel and lubricating oil. For example, an oligomer cut with a 250° F. (121° C.)-500° F. (260° C.) boiling range can be blended to jet fuel/kerosene, and oligomer cut with 400° F. (204° C.)-700° F. (371° C.) boiling range can be blended to diesel fuel. The $700^{+°}$ F. ($371^{+°}$ C.) fraction can be sent to other hydroprocessing unit in a refinery to further convert to jet and diesel fuel or sent to the lubricating oil hydrogenation unit to make a lubricating oil blend stock.

Feed Stream

The feed stream used in the process provided herein can be a pure ethylene feed or a gas stream comprising an olefin that is predominately ethylene. By predominately, it is intended that the ethylene content in the total olefin feed is in the molar majority, in certain embodiments, greater than 50%. In one embodiment, the feed stream comprises dilute ethylene gas streams such as ethylene cracker offgas, refinery fluid catalytic cracking (FCC) offgas, refinery coker unit offgas, naphtha cracking unit offgas, Fischer-Topsch (FT) synthesis unit offgas, ethylene polymerization unit offgas, and pyrolysis unit offgas.

In certain embodiments, the refinery fluid catalytic cracking (FCC) offgas is the feed stream for the processes provided herein. In one embodiment, the FCC offgas is treated by cryogenic techniques known in the art to separate a $C_2^+$ fraction.

A refinery with 70,000 barrel-per-day Fluid Catalytic Cracking (FCC) unit generates about 26 million standard cubic feet per day (MMSCFD) of offgas from the FCC unit daily and the stream contains 15 vol % ethylene. Refineries use the offgas stream as fuel to generate steam. The amount of fuel gas from the ethylene extraction unit is reduced to 21 MMSCFD, thus lowering the burden of fuel gas processing equipment. As demonstrated in Table 1 below, approximately a 19 vol % reduction of fuel gas is feasible by separating the ethylene fraction.

TABLE 1

| FCC Offgas Reduction by separating C2+ fraction | | | |
|---|---|---|---|
| | Typical FCC Offgas As-Is | After $C_2^{-+}$ Extraction | After $C_2^+$ Extraction |
| Offgas Volume, MMSCFD | 26 | 21 | 18 |
| Reduction in Fuel Gas, % | 0 (Base case) | 19 | 31 |
| Offgas Composition | | | |
| $H_2S$, ppm | 10 ppm | 0 | 0 |
| $N_2$, vol % | 6.0 | 7.4 | 8.7 |
| $O_2$, vol % | 0.1 | 0 | 0 |
| $CO_2$, vol % | 0.4 | 0 | 0 |
| CO, vol % | 0.3 | 0 | 0 |
| $H_2$, vol % | 35.8 | 44.0 | 51.7 |
| Methane, vol % | 27.5 | 33.8 | 39.7 |
| Ethane, vol % | 10.6 | 13 | 0 |
| Ethylene, vol % | 15 | 0 | 0 |
| Propane, vol % | 1.2 | 1.5 | 0 |
| Propylene, vol % | 2.5 | 0 | 0 |
| n-Butane, vol % | 0.1 | 0.1 | 0 |
| Isobutane, vol % | 0.1 | 0 | 0 |

TABLE 1-continued

FCC Offgas Reduction by separating C2+ fraction

| | Typical FCC Offgas As-Is | After $C_2^{-+}$ Extraction | After $C_2^+$ Extraction |
|---|---|---|---|
| Butene, vol % | 0.1 | 0 | 0 |
| $C_{5+}$, vol % | 0.3 | 0.2 | 0 |
| Sum | 100 | 100.0 | 100 |

In certain embodiments, the refinery fluid catalytic cracking (FCC) offgas is employed as the olefin feed stream for the processes provided herein. In one embodiment, the FCC offgas is treated by cryogenic techniques known in the art to separate a $C_2^+$ fraction.

Extracting ethylene or the $C_2^+$ olefin-only stream from FCC offgas can improve the purity of hydrogen in FCC offgas as shown in Table 2 below, from 36% to 44%. If the $C_2^+$ fraction is separated using cryogenic techniques available in industry to use for the oligomerization, the remaining $C_1-$ fraction becomes $H_2$ rich, with over 50% purity. By using advanced separation technology, such as membrane technology, it is feasible to recover additional ~9 MMSCFD of hydrogen gas from the FCC offgas, shown in Table 2.

TABLE 2

Improvement of Offgas $H_2$ Purity

| | Typical FCC Offgas As-Is | After $C_2$ Extraction | After $C_2^+$ Extraction |
|---|---|---|---|
| Offgas Volume, MMSCFD | 26 | 21 | 18 |
| Reduction in Fuel Gas, % | 0 (Base case) | 19 | 31 |
| Offgas $H_2$ purity, vol % | 35.8 | 44.0 | 51.7 |
| Available $H_2$ for Recovery, MMSCFD | 0 | 0 | 9 |

In one embodiment, the feed stream used in the processes herein comprises at least 10 weight % ethylene. In one embodiment, the feed stream comprises at least 10, 20, 30, 40, 50, 60, 70, 80 or more weight % ethylene. In one embodiment, the feed stream comprises at least 10 weight % ethylene. In one embodiment, the feed stream comprises at least 20 weight % ethylene. In one embodiment, the feed stream comprises at least 40 weight % ethylene. In one embodiment, the feed stream comprises at least 50 weight % ethylene. In one embodiment, the feed stream comprises at least 60 weight % ethylene. In one embodiment, the feed stream comprises 10-100, 10-90, 10-80, 10-10, 10-60, 10-50, 20-100, 20-90, 20-80, 20-70, 20-60, 20-50, 30-90, 30-80, 30-70, 40-100, 40-90, 40-80, 40-70, 40-60, 50-100, 50-90, 50-80 or 50-70 weight % ethylene.

In certain embodiments, the presence of normal hydrocarbons, such as n-butane or n-heptane, or diluents, such as $N_2$ or $H_2$, does not affect the conversion of ethylene by the ionic liquid catalyst in the process provided herein. In certain embodiments, the process provided herein uses an olefin feed stream with a limited amount of isoparaffins such as isobutane or isopentane or isohexane, in the feed stream; in one embodiment, the olefin feed stream comprises less than about 10 wt % of isoparaffins based upon the total weight of the feed. In certain embodiments, the amount of isoparaffins in the feed stream is less than about 9 wt %, 8 wt %, 7 wt %, 6 wt %, 5 wt %, 4 wt %, 3 wt %, 2 wt % or 1 wt % based upon the total weight of the feed. In certain embodiments, typical isoparaffins, such as isobutane or isopentane or isohexane, are present in the feed in a molar ratio of isoparaffin to olefin of 0.5 or less. In one embodiment, the molar ratio of isoparaffin to olefin is: 0.1 or less, 0.08 or less, 0.06 or less, 0.05 or less, 0.04 or less, 0.02 or less. In one embodiment, the molar ratio of isoparaffin to olefin is in the range of 0.5 to 0.01, 0.3 to 0.01, 0.1 to 0.01, or 0.05 to 0.01.

In one embodiment, the olefin feed stream used in the processes herein comprises less than 10 weight % olefins having higher carbon numbers than ethylene, wherein in one regard the higher olefins are selected from propylene and butylene, including isobutylene. In one embodiment, the feed stream comprises less than 10 weight % propylene and butylene. In one olefin feed embodiment, the molar ratio of higher carbon number olefins to ethylene in the olefin feed is 0.5 or less, 0.3 or less, 0.1 or less, 0.05 or less.

In one embodiment, the olefin feed stream comprises at least 10 weight % ethylene and less than 10 weight % propylene and butylene. In one embodiment, the feed stream comprises at least 20 weight % ethylene and less than 10 weight % propylene and butylene. In one embodiment, the feed stream comprises at least 40 weight % ethylene and less than 10 weight % propylene and butylene. In one embodiment, the feed stream comprises at least 50 weight % ethylene and less than 10 weight % propylene and butylene. In one embodiment, the feed stream comprises at least 60 weight % ethylene and less than 10 weight % propylene and butylene. In one embodiment, the feed stream comprises 10-100, 10-90, 10-80, 10-70, 10-60, 10-50, 20-100, 20-90, 20-80, 20-70, 20-60, 20-50, 30-90, 30-80, 30-70, 40-100, 40-90, 40-80, 40-70, 40-60, 50-100, 50-90, 50-80 or 50-70 weight % ethylene and less than 10 weight % propylene and butylene.

In one embodiment the feed stream contains impurities such as sulfur, nitrogen containing hydrocarbons, oxygenates, dienes, or residual trace metals which would poison typical metallocene or aluminum alkyl catalyst. In certain embodiments, the total amount of impurities in the feed stream, such as sulfur, nitrogen containing hydrocarbons, oxygenates, dienes, or residual trace metals, is less than about 0.01 wt % based in the total weight of the feed stream. The feed stream may contain 0-10 ppm Sulfur, 0-10 ppm oxygenate, 0-100 ppm dienes, 0-1 ppm residual trace metals. In certain embodiments, the ionic liquid catalyst is far more resistant to the feed impurities and the conversion of ethylene of 30 wt % or higher can be achieved.

Ionic Liquid Catalyst

The ionic liquid catalyst used in the processes provided herein is composed of at least two components which form a complex. In certain embodiments, the ionic liquid catalyst comprises a first component and a second component. In one embodiment, the first component of the ionic liquid catalyst comprises a Lewis Acid. In one embodiment, the Lewis acid is a metal halide compound selected from components such as Lewis Acidic compounds of Group 13 metals, including aluminum halides, alkyl aluminum halide, gallium halide, and alkyl gallium halide. In one embodiment, the Lewis Acidic compound is a Group 3, 4 or 5 metal halide. Exemplary compounds include $ZrCl_4$, $HfCl_4$, $NbCl_5$, $TaCl_5$, $ScCl_3$, $YCl_3$, and mixtures thereof. The periodic table by the International Union of Pure and Applied Chemistry (IUPAC), version date 22 Jun. 2007, is used for defining the Groups 3, 4, 5, and 13 metals. In one embodiment, the first component is aluminum halide or alkyl aluminum halide. In one embodiment, aluminum trichloride is the first component of the acidic ionic liquid.

In certain embodiments, the second component of the ionic liquid catalyst is an organic salt or a mixture of salts.

These salts can be characterized by the general formula Q+A−, wherein Q+ is an ammonium, phosphonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, alkyl-aryl sulfonate, and benzene sulfonate (e.g., 3-sulfurtrioxyphenyl), wherein R is an alkyl group with 1-12 carbon atoms. In one embodiment, the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment, the ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. In one embodiment, the ionic liquid catalyst is an acidic haloaluminate ionic liquid, such as an alkyl substituted pyridinium chloroaluminate or an alkyl substituted imidazolium chloroaluminate of the general formulas A and B, respectively.

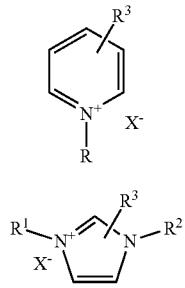

In the formulas A and B; R, $R^1$, $R^2$, and $R^3$ are each independently H, methyl, ethyl, propyl, butyl, pentyl or hexyl group, X is a chloroaluminate. In one embodiment the X is $AlCl_4^-$ or $Al_2Cl_7^-$. In the formulas A and B, R, $R^1$, $R^2$, and $R^3$ may or may not be the same. In one embodiment, the ionic liquid catalyst is N-butylpyridinium chloroaluminate.

In one embodiment, ionic liquid catalyst comprises a cation selected from alkyl-pyridinium, an alkyl-imidazolium, and a mixture thereof. In another embodiment, the ionic liquid catalyst has the general formula RR'R"NH+ $Al_2Cl_7^-$, wherein R, R' and R" are alkyl groups containing 1 to 12 carbons, and where R, R' and R" may or may not be the same.

The presence of the first component can give the ionic liquid catalyst a Franklin or Lewis acidic character. In one embodiment, the ionic liquid catalyst includes strongly Lewis acidic anions, such as $AlCl_4^-$ and $Al_2Cl_7^-$. In one embodiment, the greater the mole ratio of the first component to the second component, the greater is the acidity of the ionic liquid catalyst.

Other examples of compounds which can be used as the ionic liquid catalyst include, 1-Butyl-3-methylimidazolium hexafluorophosphate [bmim+][$PF_6^-$], Trihexyl(tetradecyl)phosphonium chloride [thtdP+][Cl−], commercially available as CYPHOS IL 101™ (Hydrocarbon soluble (hexane, toluene) Tg-56° C.), and 1-Ethyl-3-methylimidazolium tetrachloroaluminate [emim+][$AlCl_4^-$]. An ionic liquid that can be used as the second component in the ionic liquid catalyst includes Trihexyl(tetradecyl)phosphonium chloride [thtdP+][Cl−].

In one embodiment, the ionic liquid catalyst is used in about 5-30 volume % based on the total volume of the reactants. In one embodiment, the ionic liquid catalyst is used in about 5-25 volume % based on the total volume of the reactants. In one embodiment, the ionic liquid catalyst is used in about 5, 10, 15, 20, 25 or 30 volume % based on the total volume of the reactants.

In one embodiment, the ionic liquid catalyst comprises metal halides, such as $AlCl_3$, $AlBr_3$, $Al_2Cl_7$, $GaCl_3$, $GaBr_3$, $InCl_3$, and $InBr_3$. In one embodiment, the ionic liquid catalyst is N-butylpyridinium chloroaluminate ($C_5H_5NC_4H_9Al_2Cl_7$). In one embodiment, the ionic liquid catalyst has the following composition and has a density of 1.34 g/cc.

TABLE 1

| Composition of Ionic Liquid Catalyst | |
|---|---|
| ELEMENT | WT % |
| Al | 12.4 |
| Cl | 56.5 |
| C | 24.6 |
| H | 3.2 |
| N | 3.3 |

Co-Catalyst

The co-catalyst or promoter used in the processes provided herein comprises, for example, HCl or organic chloride or hydrogen halides or organic halides wherein halides include Cl, Br, I ions. In one embodiment, the co-catalyst is anhydrous HCl. When organic chloride is used as the co-catalyst with the ionic liquid catalyst, HCl may be formed in situ in the reactor during the oligomerization process. In certain embodiments, co-catalysts or promoters are Bronsted acids. A Bronsted acid is any substance that can donate an $H^+$ ion to a base. Bronsted acids are $H^+$-ion or proton donors. Examples of Bronsted acids are HCl, HBr, HI, HF, sulfuric acid, and mixtures thereof. In certain embodiments, the co-catalyst enhances the activity of the ionic liquid catalyst and improves the yield of the hydrocarbon product.

In certain embodiments, the ratio of the co-catalyst to ethylene in the olefin feed is adjusted to shift the boiling point distribution of the hydrocarbon product fractions. In one embodiment, the oligomerization conditions include a molar ratio of ethylene to the co-catalyst is between about 5 to about 75, between about 10 to about 50, or between about 10 to about 45. In one embodiment, the molar ratio of ethylene to the co-catalyst is about 10, about 13, about 15, about 20, about 22, about 25, about 30, about 35, about 38, about 40, about 41 or about 45.

Without being bound by any theory, it is believed that the Lewis acidity of the ionic liquid catalyst is enhanced by the Bronsted acidity of the HCl co-catalyst. With the catalyst combination of enhanced Lewis acidity promoted by a Bronsted acid, the ionic liquid catalyst system is able to activate ethylene molecules and the oligomerization reaction can proceed. The chain length and shifts the carbon number distribution down as well as the boiling point distribution of the hydrocarbon product.

Reaction Conditions/Reactor Unit

The oligomerization process can be conducted in a semi-batch or continuous mode. By continuous is meant a process that operates (or is intended to operate) without interruption or cessation. For example, a continuous process would be one where the reactants (such as ethylene feed, the ionic liquid catalyst and the co-catalyst) are continually introduced into one or more reactors and the product feed comprising the $C_{10}$-$C_{55}$ olefin oligomers is continually withdrawn. By semi-batch is meant a system that operates (or is intended to operate) with periodic interruption. For example, a semi-batch process to produce the $C_{10}$-$C_{55}$ olefin oligomers would be one where the reactants are continually introduced into one or more reactors and the product feed is intermittently withdrawn.

The oligomerization reaction can be conducted in any reactor that is suitable for the purpose of oligomerization of ethylene in the feedstock in the presence of an ionic liquid catalyst to obtain a hydrocarbon product comprising $C_{10}$-$C_{55}$ oligomers. Examples of reactors that can be used are continuously stirred tank reactors (CTSR), nozzle reactors (including nozzle loop reactors), tubular reactors (including continuous tubular reactors), fixed bed reactors (including fixed bed contactor reactors), and loop reactors (including static mixer loop reactors).

In one embodiment, the oligomerization process is conducted as represented in FIG. 1. With reference to FIG. 1, the ethylene feed stream, such as a dilute ethylene gas stream, is treated in feed treating unit 1 to obtain a feed stream comprising the desired amount of ethylene. The ethylene feed stream from unit 1 is fed to oligomerization reactor 2 where the oligomerization reaction takes place in presence of an ionic liquid catalyst, a co-catalyst and a solvent, such as heptane. In certain embodiments, the ethylene feed stream, the ionic liquid catalyst and the co-catalyst are introduced into oligomerization reactor 2 via separate inlet ports. In certain embodiments, the ethylene feed stream, the ionic liquid catalyst, the co-catalyst and the solvent are introduced into oligomerization reactor 2 simultaneously. In certain embodiments, the ionic liquid catalyst is mixed with the solvent before introducing the co-catalyst and ethylene feed into oligomerization reactor 2. In certain embodiments, the solvent is initially introduced into oligomerization reactor 2, followed by ionic liquid catalyst, the co-catalyst and ethylene feed stream. The ethylene feed stream is contacted with an ionic liquid catalyst and a co-catalyst in oligomerization reactor 2 under olefin oligomerization conditions.

In one embodiment, the oligomerization reaction conditions include temperatures from about 50° F. (10° C.) to about 300° F. (149° C.), such as from about 75° F. (24° C.) to about 275° F. (135° C.), from about 100° F. (38° C.) to about 250° F. (121° C.), or at about 100° F. (38° C.), 120° F. (49° C.), 125° F. (52° C.), 130° F. (54° C.), or 150° F. (66° C.). In one embodiment, the oligomerization temperature is about 122° F. (50° C.).

In certain embodiments, the oligomerization reaction is conducted under a pressure of about 100-1000 psig (689 kPa-6895 kPa). In certain embodiments, the oligomerization reaction is conducted under a pressure of about 350-700 psig (2413 kPa-4826 kPa). In certain embodiments, the oligomerization reaction is conducted under a pressure of 400-500 psig (2758 kPa-3447 kPa). In certain embodiments, the oligomerization reaction is conducted under a pressure of about 400 (2758 kPa), 450 (3103 kPa), 470 (3241 kPa) or 500 psig (3447 kPa).

In one embodiment, the oligomerization reaction occurs in less than 5 hours, less than 3 hours, less than 2 hours, or less than 1 hour. In one embodiment the oligomerization reaction occurs between 15 minutes and 150 minutes, between 30 minutes and 120 minutes, between 60 minutes and 120 minutes, or between 30 minutes and 60 minutes. In one embodiment the oligomerization reaction occurs in about 30 minutes, 60 minutes, 90 minutes, 120 minutes, 150 minutes or 180 minutes.

The effluent stream from the oligomerization reactor 2 comprising a hydrocarbon phase and spent ionic liquid catalyst enters separator 3. The hydrocarbon phase comprises the solvent and $C_{10}$-$C_{55}$ oligomer product. The hydrocarbon phase is washed with deionized water to remove the residual ionic liquid catalyst in separator 3. The ionic liquid catalyst may be fed to a catalyst regeneration unit 4 for regeneration of the ionic liquid catalyst. As an example, the ionic liquid catalyst may be regenerated by treatment with a regeneration metal, such as Al metal, or by treatment of the ionic liquid catalyst in the presence of $H_2$ with a hydrogenation catalyst. Processes for the regeneration of ionic liquid catalyst are disclosed in, for example, U.S. Pat. Nos. 7,732,364 and 7,674,739, the disclosures of which are incorporated by reference herein in their entireties.

Ionic liquid catalyst deactivation may be associated with the accumulation of conjunct polymer in the ionic liquid catalyst, which may be removed from the ionic liquid during catalyst regeneration. The rate of withdrawal of spent ionic liquid catalyst and concomitant replenishment with fresh ionic liquid, and/or the rate at which the used ionic liquid is fed to the catalyst regeneration unit may be controlled to adjust the reaction conditions within oligomerization unit 2, e.g., according to the target product(s).

In certain embodiments, the washed hydrocarbon product from separator 3 is dried with a drying agent, such as magnesium sulfate powder. The drying agent is then removed by vacuum filtration. The dried hydrocarbon phase is fed to distillation unit 5 where the hydrocarbon product is distilled to obtain the desired fraction.

In certain embodiments, the process provided herein is conducted at one or more reaction conditions selected from:
a temperature from 50° F. (10° C.) to 300° F. (149° C.);
a pressure of 100 (689 kpa) to 1000 psig (6895 kpa);
a reaction residence time of 15 to 150 minutes; and
a sufficient mixing to provide effective contact between the ionic liquid catalyst and the ethylene.

In certain embodiments, provided herein is a process for ethylene oligomerization in the presence of an ionic liquid catalyst and a co-catalyst to produce a hydrocarbon product comprising hydrocarbons predominantly boiling in jet, diesel and base oil product range.

In one embodiment, provided herein is a hydrocarbon product prepared by the processes disclosed herein. In one embodiment, the hydrocarbon yield is greater than 30% by weight of the ethylene feed.

Hydrocarbon Product

In certain embodiments, the product obtained by the process provided herein comprises $C_{10}$-$C_{55}$ oligomers in an amount of at least about 30 weight %. In certain embodiments, the product comprises $C_{10}$-$C_{55}$ oligomers in an amount of at least about 40 weight %. In certain embodiments, the product comprises $C_{10}$-$C_{55}$ oligomers in an amount of at least about 50 weight %. In certain embodiments, the product comprises $C_{10}$-$C_{55}$ oligomers from about 30 weight % to about 99 weight %. In certain embodiments, the product comprises $C_{10}$-$C_{55}$ oligomers from about 40 weight % to about 95 weight %. In certain embodiments, the product comprises $C_{10}$-$C_{55}$ oligomers from about 40 weight % to about 90 weight %. In certain embodiments, the product comprises $C_{10}$-$C_{55}$ oligomers from about 45 weight % to about 99 weight %. In certain embodiments, the product comprises $C_{10}$-$C_{55}$ oligomers from about 40-99, 45-95, 50-95, 50-90, 60-95, 60-90, 70-95, 70-90, 75-95 or 75-90 weight %. In one embodiment, the product comprises $C_{10}$-$C_{55}$ oligomers from about 45, 50, 55, 60, 65, 68, 70, 75, 77, 80, 85, 90, 95 to 99 weight %.

In certain embodiments, the product obtained by the process provided herein has a carbon number distribution range of $C_{10}$-$C_{55}$. In certain embodiments, the product has a carbon number distribution range of $C_{12\text{-}55}$, $C_{10\text{-}52}$, $C_{10\text{-}50}$, $C_{12\text{-}50}$, $C_{14\text{-}40}$ or $C_{14\text{-}36}$.

In certain embodiments, the product obtained by the process provided herein has an average carbon number of 15-40. In certain embodiments, the product has an average carbon number of 21-34. In certain embodiments, the product has an average carbon number of 21, 23, 25 or 34. In certain embodiments, the product has an average carbon number of 20, 21, 22, 23, 24, 25, 26, 27, 28, 29, 30, 31, 32, 33 or 34.

In certain embodiments, the product obtained by the process provided herein comprises hydrocarbons having a Branching Index (BI) of 45-70%. In certain embodiments, the product comprises hydrocarbons having a BI of 48-65%. In certain embodiments, the product comprises hydrocarbons having a BI of 50-63%. In certain embodiments, the product comprises hydrocarbons having a BI of about 45%, 48%, 50%, 51%, 52%, 53%, 54%, 55%, 56%, 57%, 58%, 59%, 60%, 61%, 62%, 63%, 64% or 65%.

In certain embodiments, the ratio of $CH_3$ and $CH_2$ hydrogen in the product obtained by the process provided herein is 1.2-2.2. In certain embodiments, the ratio of $CH_3$ and $CH_2$ hydrogen in the product obtained by the process provided herein is 1.3-2.2, 1.3-2.1, 1.2-2.1, 1.3-2, or 1.4-2. In certain embodiments, the ratio of $CH_3$ and $CH_2$ hydrogen in the product obtained by the process provided herein is 1.2, 1.3, 1.4, 1.5, 1.6, 1.7, 1.8, 1.9, 2, 2.1 or 2.2.

In certain embodiments, the product obtained by the process provided herein has less than 2 mole % olefinic hydrogen by $^1$H NMR. In certain embodiments, the product obtained by the process provided herein has an olefinic hydrogen by $^1$H NMR in the range of 0.1-1.5 mole %. In certain embodiments, the product has an olefinic hydrogen by $^1$H NMR in the range of 0.2-1.3 mole %, 0.3-1.2 mole %, 0.4-1 mole % or 0.5-0.8 mole %.

In certain embodiments, the product obtained by the process provided herein has a paraffinic $CH_3$ hydrogen by $^1$H NMR in the range of 45-70 mol %. In certain embodiments, the product obtained by the process provided herein has a paraffinic $CH_3$ hydrogen by $^1$H NMR in the range of 50-65 mol %. In certain embodiments, the product has a paraffinic $CH_3$ hydrogen by $^1$H NMR in the range of 52-64 mol %.

In certain embodiments, the product obtained by the process provided herein has a paraffinic $CH_2$ hydrogen by $^1$H NMR in the range of 25-45 mol %. In certain embodiments, the product obtained by the process provided herein has a paraffinic $CH_2$ hydrogen by $^1$H NMR in the range of 28-40 mol %. In certain embodiments, the product has a paraffinic hydrogen ($CH_2$) by $^1$H NMR in the range of 30-40 mol %.

In certain embodiments, the product obtained by the process provided herein has a paraffinic hydrogen (CH+allylic) by $^1$H NMR in the range of 5-15 mol %. In certain embodiments, the product obtained by the process provided herein has a paraffinic hydrogen (CH+allylic) by $^1$H NMR in the range of 7-9 mol %.

In certain embodiments, the product obtained by the process provided herein has an aromatic hydrogen by $^1$H NMR less than about 0.1 mole % or less than about 0.05 mole %.

In certain embodiments, the product obtained by the process provided herein has a bromine number of 1-10, 2-8, 2-6, or 2-4. In certain embodiments, the product has bromine number of 1, 1.5, 2, 2.5, 2.8, 2.9, 3, 3.5, 4, 4.5, 5, 5.5, 6, 6.5, 7, 7.5, 8, 8.5, 9, 9.5 or 10. Bromine number can be measured by ASTM D1159-07(2012).

In certain embodiments, the hydrocarbon product obtained by the process provided herein has a carbon number range of $C_{10\text{-}55}$, an average carbon number of 20-40, a BI of 45-70%, the ratio of $CH_3$ and $CH_2$ hydrogen of 1.2-2.2, olefinic hydrogen in the range of 0.1-1.5 mole %, an aromatic hydrogen less than 0.1 mole %, and a bromine number of 1-10. In one embodiment, the hydrocarbon product obtained by the process provided herein has a carbon number range of $C_{10\text{-}55}$, an average carbon number of 21-36, a BI of 50-63%, the ratio of $CH_3$ and $CH_2$ hydrogen of 1.2-2.0, an olefinic hydrogen in the range of 0.4-1 mole %, an aromatic hydrogen less than 0.05 mole %, and a bromine number of 1-5.

In certain embodiments, the product obtained by the process provided herein comprises from about 40 to about 90 weight % of $C_{10}$-$C_{55}$ oligomers having boiling points in the jet and diesel fuel range, i.e. 250° F.-700° F. (121-371° C.). In certain embodiments, the product comprises from about 45 to about 85 weight % of $C_{10}$-$C_{55}$ oligomers having boiling points in the jet and diesel fuel range. In one embodiments the product comprises about 47, about 50, about 65, about 69, about 75, about 80 or about 85 weight % of $C_{10}$-$C_{55}$ oligomers having boiling points in the jet and diesel fuel range.

In certain embodiments, the product obtained by the process provided herein comprises from about 5 to about 50 weight % of $C_{10}$-$C_{55}$ oligomers having boiling points in the lubricating oil range, i.e. about 650° F. (343° C.) or higher. In certain embodiments, the product comprises from about 5 to about 35 weight % of $C_{10}$-$C_{55}$ oligomers having boiling points in the lubricating oil range. In certain embodiments, the product comprises about 5, 8, 10, 15, 20, 25, 28, 30, 35, 40, 45, 48 or 50 weight % of $C_{10}$-$C_{55}$ oligomers having boiling points in the lubricating oil range.

In certain embodiments, the product obtained by the process provided herein comprises from about 1 to about 10 weight % of $C_{10}$-$C_{55}$ oligomers having boiling points in the range from 215-250° F. (102-121° C.). In certain embodiments, the product obtained by the process provided herein comprises from about 2 to about 7 weight % of $C_{10}$-$C_{55}$ oligomers having boiling points in the range from 215-250° F. (102-121° C.).

In certain embodiments, the product obtained by the process provided herein comprises a $C_{10}$-$C_{55}$ oligomer fraction having boiling points between about 250° F.-500° F. (121-260° C.) and a flash point of about 100° F.-162° F. (38-72° C.). In certain embodiments, the product obtained by the process provided herein comprises a $C_{10}$-$C_{55}$ oligomer fraction having boiling points between about 250° F.-500° F. (121-260° C.) and a flash point of about 105° F., 110° F., 111° F., 115° F. or 120° F. (41, 43, 44, 46 or 49° C.).

In certain embodiments, the product obtained by the process provided herein comprises a $C_{10}$-$C_{55}$ oligomer fraction having boiling points between about 250° F.-500° F. (121-260° C.) and a freeze point of lower than −40° F. (−40° C.). Freeze point can be measured by ASTM D1015-05 (R2010). In certain embodiments, the product obtained by the process provided herein comprises a $C_{10}$-$C_{55}$ oligomer fraction having boiling points between about 250° F.-500° F. (121-260° C.) and a cloud point of lower than −40° F. (−40° C.). Cloud point can be measured by ASTM D2500-11.

In certain embodiments, the product obtained by the process provided herein comprises a $C_{10}$-$C_{55}$ oligomer fraction having boiling points between about 250° F.-500° F. (121-260° C.) and a cetane index of above 40. Cetane index can be determined by ASTM D976-06(R2011) or ASTM D4737-10. In certain embodiments, the product obtained by the process provided herein comprises a $C_{10}$-$C_{55}$ oligomer fraction having boiling points between about 250° F.-500° F. (121-260° C.) and a cetane index of about 40-55. In certain embodiments, the product obtained by the process provided herein comprises a $C_{10}$-$C_{55}$ oligomer fraction having boiling points between about 250° F.-500° F. (121-260° C.) and a cetane index of about 40, 45, 48.2, 50 or 55.

In certain embodiments, the product obtained by the process provided herein comprises a $C_{10}$-$C_{55}$ oligomer fraction having boiling points between about 250° F.-500° F. (121-260° C.) and a specific gravity of about 0.7-0.9. In certain embodiments, the product obtained by the process provided herein comprises a $C_{10}$-$C_{40}$ oligomer fraction having boiling points between about 250° F.-500° F. (121-260° C.) and a specific gravity of about 0.7, 0.75 or 0.76. Specific gravity can be measured by ASTM D1217-12.

In certain embodiments, the hydrocarbon product obtained by the process provided herein comprises a $C_{10}$-$C_{55}$ oligomer fraction having boiling points between about 250° F.-500° F. (121-260° C.) and a sulfur content less than 5 ppm.

In certain embodiments, the hydrocarbon product obtained by the process provided herein comprises a $C_{10}$-$C_{55}$ oligomer fraction having boiling points between about 500° F.-700° F. (260-371° C.) and a flash point of about 200-300° F. (93-149° C.). In certain embodiments, the hydrocarbon product obtained by the process provided herein comprises a $C_{10}$-$C_{55}$ oligomer fraction having boiling points between about 500° F.-700° F. (260-371° C.) and a flash point of about 265° F., 270° F., 273° F. or 275° F. (129, 132, 134, or 135° C.).

In certain embodiments, the hydrocarbon product obtained by the process provided herein comprises a $C_{10}$-$C_{55}$ oligomer fraction having boiling points between about 500° F.-700° F. (260-371° C.) and a freeze point of less than −40° F. (−40° C.). In certain embodiments, the hydrocarbon product obtained by the process provided herein comprises a $C_{10}$-$C_{40}$ oligomer fraction having boiling points between about 500° F.-700° F. (260-371° C.) and a cloud point of less than −40° F. (−40° C.).

In certain embodiments, the hydrocarbon product obtained by the process provided herein comprises a $C_{10}$-$C_{55}$ oligomer fraction having boiling points between about 500° F.-700° F. (260-371° C.) and a cetane index of above 40. In certain embodiments, the hydrocarbon product obtained by the process provided herein comprises a $C_{10}$-$C_{55}$ oligomer fraction having boiling points between about 500-700° F. (260-371° C.) and a cetane index of about 45-65. In certain embodiments, the hydrocarbon product obtained by the process provided herein comprises a $C_{10}$-$C_{55}$ oligomer fraction having boiling points between about 500° F.-700° F. (260-371° C.) and a cetane index of about 50, 55, 56.8, or 60.

In certain embodiments, the hydrocarbon product obtained by the process provided herein comprises a $C_{10}$-$C_{55}$ oligomer fraction having boiling points between about 500° F.-700° F. (260-371° C.) and a specific gravity of about 0.7-0.9. In certain embodiments, the hydrocarbon product obtained by the process provided herein comprises a $C_{10}$-$C_{55}$ oligomer fraction having boiling points between about 500° F.-700° F. (260-371° C.) and a specific gravity of about 0.75, 0.8 or 0.85.

In certain embodiments, the hydrocarbon product obtained by the process provided herein comprises a $C_{10}$-$C_{55}$ oligomer fraction having boiling points between about 500° F.-700° F. (260-371° C.) and a sulfur content less than 5 ppm.

In certain embodiments, the hydrocarbon product obtained by the process provided herein comprises a $C_{10}$-$C_{55}$ oligomer fraction having boiling points greater than 700° F. (371° C.) and pour point lower than 14° F. (−10° C.). Pour point can be measured by ASTM D5950-14. In certain embodiments, the hydrocarbon product obtained by the process provided herein comprises a $C_{10}$-$C_{55}$ oligomer fraction having boiling points greater than 700° F. (371° C.) and a pour point of about 10° F. (−23° C.) to about 10° F. (−12° C.). In certain embodiments, the hydrocarbon product obtained by the process provided herein comprises a $C_{10}$-$C_{55}$ oligomer fraction having boiling points greater than 700° F. (371° C.) and a pour point of about −4.5° F., −5° F., −5.5° F., −5.8° F. or −6° F. (or −20, −20.5, 21, −21.5, or −22° C.).

In certain embodiments, the hydrocarbon product obtained by the process provided herein comprises a $C_{10}$-$C_{55}$ oligomer fraction having boiling points between about 500° F.-700° F. (260-371° C.) and a cloud point of less than 14° F. (−10° C.).

In certain embodiments, the hydrocarbon product obtained by the process provided herein comprises a $C_{10}$-$C_{55}$ oligomer fraction having boiling points greater than 700° F. (371° C.) and a kinematic viscosity of about 500-600 mm$^2$/s at 40° C. In certain embodiments, the hydrocarbon product obtained by the process provided herein comprises a $C_{10}$-$C_{55}$ oligomer fraction having boiling points greater than 700° F. (371° C.) and a kinematic viscosity of about 550, 555, 558, 560 or 565 mm$^2$/s at 40° C. Kinematic viscosity can be measured by ASTM D445-15.

In certain embodiments, the hydrocarbon product obtained by the process provided herein comprises a $C_{10}$-$C_{40}$ oligomer fraction having boiling points greater than 700° F. (371° C.) and a kinematic viscosity of about 15-60 mm$^2$/s at 100° C. In certain embodiments, the hydrocarbon product obtained by the process provided herein comprises a $C_{10}$-$C_{55}$ oligomer fraction having boiling points greater than 700° F. (371° C.) and a kinematic viscosity of about 22, 24, 24.8 or 30 mm$^2$/s at 100° C.

In certain embodiments, the hydrocarbon product obtained by the process provided herein comprises a $C_{10}$-$C_{55}$ oligomer fraction having boiling points greater than 700° F. (371° C.) and a viscosity index of about 30-100. In certain embodiments, the hydrocarbon product obtained by the process provided herein comprises a $C_{10}$-$C_{55}$ oligomer fraction having boiling points greater than 700° F. (371° C.) and a viscosity index of about 40 or 60 or 80 or 100. Viscosity index can be measured by ASTM D2270-10 (E2011).

In certain embodiments of the process provided herein, an ethylene stream from FCC offgas is converted into about 130 ton (about 1.179e+005 kilograms) of hydrocarbon product per day assuming 100% conversion of ethylene. Thus, assuming 330 days of operating time, annual yield of up to 42,900 ton (3.892e+007 kilograms)/year of hydrocarbon product useful for jet fuel, diesel and lubricant blending stock can be obtained using the process provided herein.

The following examples are presented to exemplify embodiments of the invention but are not intended to limit the invention to the specific embodiments set forth. Unless indicated to the contrary, all parts and percentages are by weight. All numerical values are approximate. When numerical ranges are given, it should be understood that embodiments outside the stated ranges may still fall within the scope of the invention. Specific details described in each example should not be construed as necessary features of the invention.

EXAMPLES

The following examples are intended for illustrative purposes only and do not limit in any way the scope of the present invention.

N-butylpyridinium chloroaluminate ($C_5H_5NC_4H_9Al_2Cl_7$) was the ionic liquid catalyst used in the examples below. This ionic liquid catalyst had the following composition and had a density of 1.34 g/cc.

TABLE 3

Composition of Ionic Liquid Catalyst

| ELEMENT | WT % |
|---|---|
| Al | 12.4 |
| Cl | 56.5 |
| C | 24.6 |
| H | 3.2 |
| N | 3.3 |

Comparative Example 1

Ethylene Oligomerization without Co-Catalyst in Semi-Batch Mode

Pure chemical grade ethylene gas (>99.5% purity) was used in the reaction feed for this example.

In a glove box, 54 g of n-heptane and 72 g of ionic liquid catalyst were added to a 300-cc autoclave reactor. Then the autoclave was taken out of the glove box and the mixture was stirred at 1,200 RPM and the autoclave was heated to 50° C. (122° F.). While stirring, ethylene gas was fed into the autoclave using a flow controller setting at 1,000 cc/min with a constant back pressure of 500 psig (3447 kPa). Due to high vapor pressure of ethylene gas and very low conversion of ethylene, the reactor was filled with ethylene gas and reached to 500 psig (3447 kPa) rather rapidly, thus continuing steady addition of ethylene was difficult. For a duration of 1 hour, only 35 g of ethylene (30 L of gas) was fed to the reactor. During the course of ethylene addition, the temperature was controlled at 50° C. (122° F.). After 1 hour of ethylene gas addition, the autoclave was continued to stir at 1,200 RPM for 30 more minutes for conversion of ethylene to oligomerized olefins.

During the reaction, the autoclave reactor contained a multi-phase mixture, i.e. ethylene and HCl in gas phase and two immiscible liquid phases containing (1) ionic liquid catalyst and (2) liquid hydrocarbon product and heptane solvent. The n-heptane solvent was added to improve the contact between ethylene in the gas phase and the ionic liquid catalyst. Based on the final volume of reactor with the internal volume of 280 cc, the above addition conditions corresponded to 20 vol % ionic liquid catalyst and 30 vol % of heptane. A summary of the process conditions is provided in Table 4.

After the 1 hour hold, the autoclave was degassed to the atmospheric pressure, and the reaction product was separated using a glass separatory funnel into a hydrocarbon phase containing n-heptane and an oligomer product, and an ionic liquid catalyst phase. The hydrocarbon phase was washed with deionized water to remove the residual ionic liquid catalyst. The washed hydrocarbon product was dried with magnesium sulfate powder drying agent, and then the magnesium sulfate drying agent was removed by vacuum filtration using a 0.7 micron filter paper. The dried hydrocarbon phase was analyzed by simulated distillation test (ASTM D2887-14 Method). The simulated distillation data was corrected to subtract the heptane solvent and then re-normalized to obtain the boiling point distribution of the oligomer product only. The oligomer yield was very low, less than 4.5 g of oligomer product was obtained. The distillation results are provided in Table 4 and FIG. 2.

Example 2

Improved Ethylene Oligomerization with t-Butyl Chloride Promoter in Semi-Batch Mode The same equipment, reagents and procedure as in Example 1 were used in this example except for an addition of t-butyl chloride promoter to the autoclave. In a glove box, 54 g of n-heptane, 72 g of ionic liquid catalyst, and 6.3 g of t-butyl chloride were added to a 300-cc autoclave reactor. Then the autoclave was taken out of the glove box and the rest of the experimental procedure was identical to the Example 1. The molar ratio of ethylene to organic chloride was 36.

For this example, 47 g of ethylene (40 L of gas) was fed to the reactor for the duration of 1 hour and 17.4 g of product was obtained. The process conditions, product yield, and product boiling point distribution are reported in Table 4.

Example 3

Optimized Ethylene Oligomerization in Semi-Batch Mode with HCl Co-Catalyst

The same equipment, reagents and procedure as described in Example 1 were used in this example except for an addition of anhydrous HCl gas to the autoclave.

As in Example 1, in a glove box, 54 g of n-heptane and 72 g of ionic liquid were added to a 300-cc autoclave reactor. The autoclave was taken out of the glove box. About 7.2 g of anhydrous HCl gas from a lecture bottle was added to the reactor and the mixture was stirred at 1,200 RPM. The autoclave was heated to 122° F. (50° C.) before addition of the ethylene feed. The rest of the procedure was the same as used for Example 1.

In this experiment, ethylene gas was reacted rapidly to form a liquid hydrocarbon product and created headroom for fresh ethylene gas addition. While the back pressure regulator was set at 500 psig (3447 kPa), the pressure was maintained less than 500 psig (3447 kPa) for the entire duration indicating that the ethylene gas was converted almost completely. A total of 74 g of ethylene (63 L of gas) was fed to the reactor during the 1-hour addition period. The molar ratio of ethylene to HCl at the end of the reaction was 13. Yield of the product was about 37 g.

The process conditions and product boiling point distribution of the Examples 1 through 3 are summarized in Table 4.

TABLE 4

Ethylene Oligomerization with Ionic Liquid Catalyst

| | Example 1 (comparative) | Example 2 | Example 3 | Example 4 | Example 5 |
|---|---|---|---|---|---|
| Process Conditions | Semi-Batch | Semi-Batch | Semi-Batch | Continuous | Continuous |
| Olefin Source | Ethylene | Ethylene | Ethylene | Ethylene | Ethylene |
| Temperature, °F. | 122 | 122 | 122 | 122 | 122 |
| Final Pressure, Psig | 500 | 500 | 470 | 400 | 400 |
| Vol % of Ionic Liquid Cat | 20 | 20 | 20 | 20 | 20 |
| Chloride Source (promoter or co-catalyst) | None | t-butyl chloride | HCl | HCl | HCl |
| Olefin/Chloride Molar Ratio | No HCl | 36 | 13 | 38 | 20 |
| Simulated Distillation, °F. | | | | | |
| Initial Boiling Point (IBP) | 215 | 214 | 212 | 172 | 175 |
| °F. At 10 Wt % | 322 | 278 | 258 | 409 | 337 |
| °F. At 30 Wt % | 481 | 348 | 345 | 575 | 458 |
| °F. At 50 Wt % | 625 | 429 | 420 | 713 | 570 |
| °F. At 70 Wt % | 751 | 539 | 516 | 840 | 693 |
| °F. At 90 Wt % | 867 | 732 | 671 | 964 | 873 |
| Final Boiling Point (FBP) | 944 | 928 | 888 | 1025 | 1016 |
| Boiling Point Distribution Of Product | | | | | |
| % (215-250° F.) | 9 | 15 | 7 | 1 | 2 |
| % (250-700° F.) | 58 | 74 | 85 | 47 | 69 |
| % (700-1000° F.) | 33 | 11 | 8 | 48 | 28 |
| % (1000-1500° F.) | 0 | 0 | 0 | 4 | 1 |
| Ethylene Conversion or Yield, % (a) | 12 | 37 | 50 | 68 | 77 |
| Jet + Diesel Selectivity, % (b) | 58 | 74 | 85 | 47 | 69 |
| PPM Chloride In Oligomer | 260 | — | 640 | 190 | — |

(a): % Yield = weight of product/weight of ethylene feed × 100 = ethylene conversion
(b): % Jet + Diesel Product selectivity = (weight of product in 250-700° F. boiling range)/total product.

As seen from the data in Table 4, the ethylene oligomerization reaction with the ionic liquid catalyst without a co-catalyst converted only 12 mol % of the ethylene fed to the reactor to a product (Example 1). It was found that ethylene was not very reactive for olefin oligomerization with the ionic liquid catalyst alone.

When t-butyl chloride was added to the ionic liquid catalyst (Example 2), a significant improvement in ethylene conversion and oligomer yield were observed. Compared to Example 1, the oligomer yield was increased from 12.8% to 37%. The reactivity of the ionic liquid catalyst was increased with addition of t-butyl chloride and more ethylene was consumed for the oligomerization.

While t-butyl chloride promoter improved the catalyst activity, it was found that addition of HCl was even more effective in increasing the reactivity of the ionic liquid catalyst and even higher conversions of ethylene and oligomer yields were achieved in Example 3. When HCl was added, as shown in Example 3, an improvement in catalyst activity was observed and a greater percentage of ethylene was converted to oligomers. This observation indicates that, in certain embodiments, HCl co-catalyst enhances the activity of the ionic liquid catalyst, and the combined catalyst system of HCl and ionic liquid is able to convert ethylene to hydrocarbon products in gasoline, jet, diesel and lubricant boiling ranges.

Figure 2:
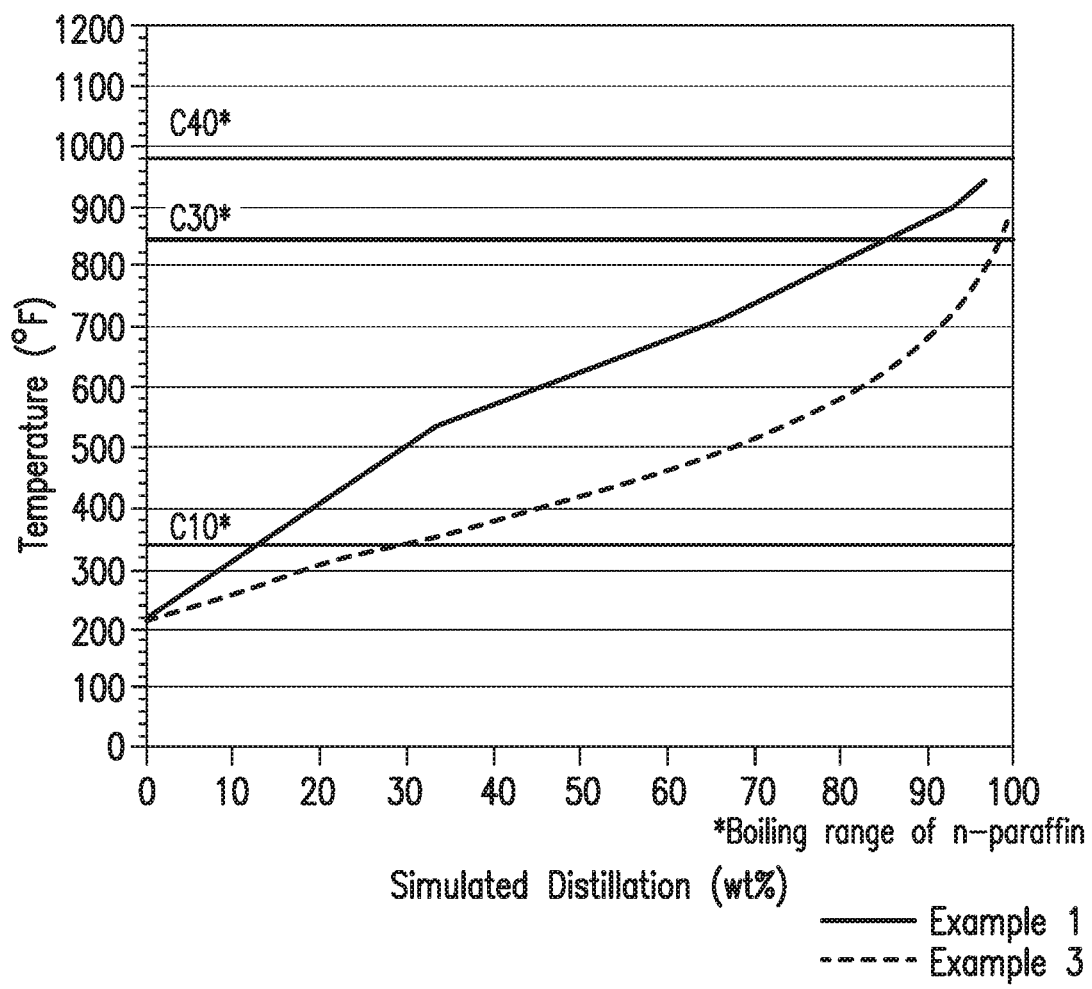
FIG. 2 provides boiling point distribution of hydrocarbon products prepared in a process provided herein.

A simulated distillation plot of the hydrocarbon products from Examples 1 and 3 are illustrated in FIG. 2. The simulated distillation plot along with data in Table 4 demonstrate that the HCl addition not only improves ethylene conversion and oligomer yield, but also shifts the boiling point distribution of the hydrocarbon product towards the jet and diesel boiling range. The hydrocarbon product in Example 3 showed much improved selectivity for the jet+diesel product (85 wt %) as compared to the Example 1 that showed 58 wt % jet+diesel product selectivity. The results here demonstrate that in certain embodiments, the boiling point distribution of the product can be adjusted by controlling the HCl co-catalyst content.

Example 4

Ethylene Oligomerization in Continuous Mode

A continuous microunit with 100 cc autoclave reactor was used to oligomerize pure chemical grade ethylene gas to produce a hydrocarbon product in a continuous manner.

A 100-cc reactor was filled initially with heptane. About 0.2 g/min of ionic liquid, about 5.0 cc/min anhydrous HCl gas and about 190 cc/min ethylene gas were added in a continuous manner while the reactor was maintained at 122° F. (50° C.) temperature, 400 psig (2758 kPa) of outlet pressure and 1,200 RPM of agitation. Assuming ethylene and HCl were dissolved into the liquid hydrocarbon phase in the reactor, these conditions corresponded to 20 vol % ionic liquid catalyst and a reaction residence time of 120 minutes. The ethylene to HCl molar ratio was 38.

The reactor effluent was de-pressured to the atmospheric pressure and separated continuously with a 3-phase separator into a gas phase, a hydrocarbon phase containing a product and an ionic liquid phase.

The hydrocarbon phase was washed in batches with an equal volume of deionized water to remove the residual ionic liquid catalyst. The washed hydrocarbon product was dried with magnesium sulfate powder drying agent, and the magnesium sulfate drying agent was removed by vacuum filtration using a 0.7 micron filter paper. The dried oligomer was analyzed by simulated distillation test (ASTM D2887-14 Method).

The results, summarized in Table 4, show that 68 mol % conversion of ethylene to hydrocarbon product was achieved and the product had 47 wt % jet+diesel product selectivity.

Example 5

Optimized Ethylene Oligomerization in Continuous Mode

The same microunit as in Example 4 was used for this example except a higher amount of HCl co-catalyst was added.

As in Example 4, a 100-cc reactor was filled initially with heptane. About 0.2 g/min of ionic liquid, about 9.5 cc/min anhydrous HCl gas and about 190 cc/min ethylene gas were added in a continuous manner while the reactor was maintained at 122° F. (50° C.) temperature, 400 psig (2758 kPa) of outlet pressure and 1,200 RPM of agitation. These conditions corresponded to 20 vol % ionic liquid catalyst and a residence time of 120 minutes assuming ethylene and HCl were dissolved in a liquid phase in the reactor. The ethylene to HCl molar ratio was 20. The rest of the procedure was the same as in Example 4. The results, summarized in Table 4, show that 77 mol % conversion of ethylene to hydrocarbon product was achieved and the product had 69 wt % jet+diesel product selectivity.

The data in Table 4 indicate that the continuous process (Example 4) allowed higher conversion of ethylene than the semi-batch mode (Example 3) (50 mol % conversion vs. 68% conversion). However, the Example 4 made heavier product than the semi-batch process in Example 3 as evidenced by higher 90 wt % boiling point (671 vs. 964° F.) and the final boiling point (888 vs. 1025° F.). Correspondingly, Example 4 had poorer jet+diesel selectivity than Example 3 (85% vs. 47% selectivity). These results suggest that the continuous process needs further optimization to increase the product selectivity.

In Example 5, by adding a higher amount of HCl, the ethylene conversion was increased even further from Example 4 and higher product yield was obtained (from 68% to 77%). In addition, the product from Example 5 showed an improved jet+diesel product selectivity of 69%. Compared with Example 4, this Example 5 of the improved continuous process made less heavy product as evidenced by lower 90 wt % boiling point (964° F. vs. 873° F.) and the final boiling point (1025° F. vs. 1016° F.).

Example 6

Analysis of Hydrocarbon Product for Molecular Weight Determination

Waters GCT Field Ionization Mass Spectrometer (FIMS) with FD/FI source analysis was used to determine the molecular weight distribution of the product. FIMS analysis is a soft ionization technique that is effective in determining the carbon number distribution of the molecules in a mixture. The analysis assumes a similar ionization response for all olefins. The injector temperature was maintained at 320° C. and the helium carrier gas flow rate was 1 mL/min.

Figure 3:
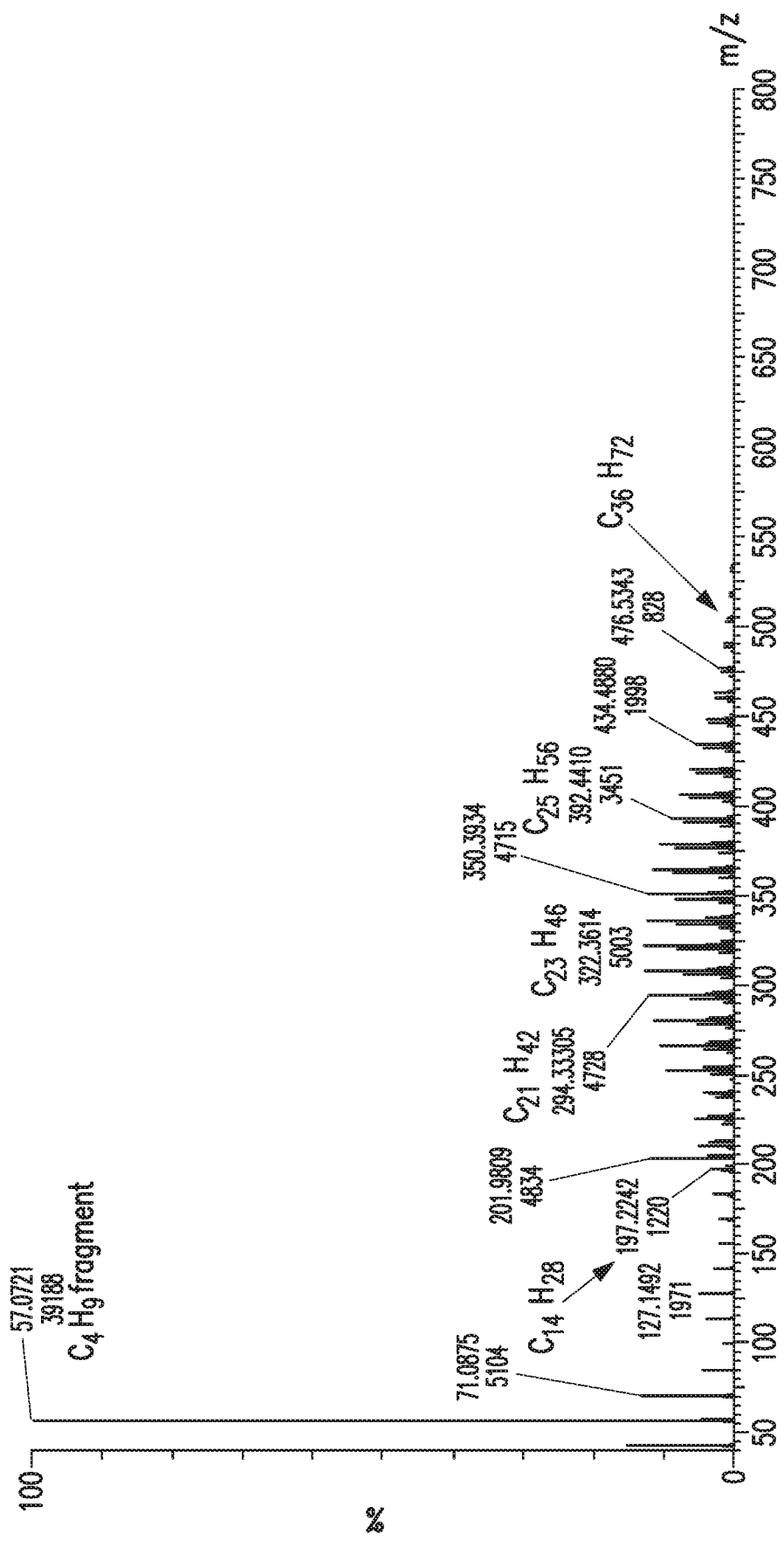
FIG. 3 provides a FIMS spectrum of the hydrocarbon product prepared in a process provided herein.

FIG. 3 provides the FIMS spectrum of the product prepared from ethylene from Example 3. A substantial fragmentation of oligomer molecules to light components of less than $C_{10}$ was observed by FIMS. An intense $C_4H_9$ fragment peak in the FIMS spectrum is observed and is likely a t-butyl cationic species from fragmentation of prevalent $C_4$ alkyl functional groups in the oligomer made from ethylene.

Example 7

Analysis of Hydrocarbon Product with NMR Method

Proton ($^1$H) Nuclear Magnetic Resonance (NMR) spectra was recorded at 400 MHz on a Bruker instrument and chemical shifts were reported in ppm on a δ scale referenced to residual solvent (CHCl$_3$ in CDCl$_3$: 7.27). The integral of the methyl groups is defined as the peak area from δ=0.5-1.0 ppm, integral of the methylene groups are defined as the peak area from δ=1.0-1.4, and integral of methine and allylic protons from δ=1.4-2.1 ppm.

The branching index (BI) of the product was determined using proton ($^1$H) NMR peak integration areas. BI is defined as the % ratio of integral values of the methyl group (CH$_3$) protons compared to the sum of the methylene (—CH$_2$—), methinyl (—CH—) and methyl (—CH$_3$) group protons (equation 1). Allylic (H—CR$_2$—CR=CR$_2$) and methinyl protons (H—CR$_3$) overlap slightly and these two species are grouped together.

Branching Index=ƒmethyl/(Σƒmethyl+ƒmethylene+ƒmethine)×100%   Equation 1. Branching index (BI)

Compositional analyses of the products made from ethylene are summarized in Table 5.

TABLE 5

Properties of Ethylene Oligomer Products

|  | Example 3 | Example 4 |
|---|---|---|
| Olefin Feed Source | Ethylene | Ethylene |
| FIMS Analysis For Carbon Number Ranges | | |
| Carbon Number Range | 14-36 | 10-52 |
| Average Carbon Number | 23 | 34 |
| Structural Analysis By $^1$H NMR (Mol %) | | |
| Paraffinic CH$_3$ Hydrogens | 61.2 | 53.1 |
| Paraffinic CH$_2$ Hydrogens | 30.3 | 38.1 |
| Paraffinic CH + Allylic Hydrogens | 8.0 | 8.0 |
| Olefinic Hydrogens | 0.5 | 0.8 |
| Aromatic Hydrogens | 0 | 0 |
| Sum | 100 | 100 |
| NMR Branching Index | 61.5 | 53.5 |
| CH$_3$/CH$_2$ Hydrogen Ratio | 2.0 | 1.4 |
| % Aromatic Protons | 0 | 0 |
| Bromine Number | 2.9 | — |

FIMS data in Table 4 and FIG. 3 indicate that the hydrocarbon product of Example 3 had the average carbon number of 23 and the carbon number distribution ranging from $C_{14}$ to $C_{36}$. The hydrocarbon product from Example 4 had the average carbon number of 34 and the carbon number distribution ranging from $C_{14}$ to $C_{52}$. The process provided herein converted ethylene to jet, diesel, and lubricant blending stock boiling range hydrocarbon products.

$^1$H NMR of the product indicated that the process provided herein generated a highly methyl-branched hydrocarbon product as evidenced by the very high Branching Index of 53.5-61.5%. For comparison, the BI of a saturated, non-branched n-$C_{23}$ product would be 20.6%. The hydrocarbon products had the CH$_3$/CH$_2$ hydrogen ratio of 1.4-2.0, and the CH hydrogen was only 8%. These suggest that the ethylene oligomer from the process provided herein had mainly methyl group side chains, and the back-bone of the hydrocarbon chain was made of mostly methylene group (—C—CH$_2$—C—) and had only a limited amount of tri-alkyl substituted methine group (—C—CHR—C—). The ethylene oligomer contained no aromatic hydrogen and was an excellent blending stock for jet and diesel fuels.

The NMR results indicate that the methyl groups were likely attached to form tetra-substituted carbon, (—C—C(CH$_3$)$_2$—C—). This is consistent with the intense C$_4$ fragmentation moieties observed in FIMS. Based on this, it was concluded that ethylene oligomer's primary building block was made of alternating methylene and tetra-substituted carbons, (—CH$_2$—C(CH$_3$)$_2$—), and this would generate intense t-butyl moieties in FIMS.

The olefinic hydrogen content of the product was very low, 0.5-0.8 mol %. If the ethylene oligomerization process instead generated olefinic product, then the expected olefinic hydrogen content would be about 3-4%. This was an indication that the ethylene oligomerization process provided herein produced substantial amounts of saturated hydrocarbons. The measured bromine number of 2.9 confirmed that the product was substantially saturated molecules. While not wishing to be bound by a theory, the presence of saturated molecules and low bromine number of the product suggests that the product was made by ethylene oligomerization as well as some saturation i.e. hydrogenation. Potential hydrogen sources for saturation could be HCl, hydrogens formed due to coke or conjunct polymer formation, or hydrogens in the hydrocarbon solvent. It appeared that the highly acidic ionic liquid and HCl co-catalyst system was able to provide a hydrogen or saturating material source (Cl for example) to the oligomer.

Example 8

Product Properties of Jet, Diesel and Lubricating Oil Blending Components

The product from Example 4 was distillated in a laboratory into light distillate (kerosene and jet), heavy distillate (diesel) and lubricating oil fractions. Product properties of each fraction are summarized in Table 6.

TABLE 6

Product Properties of Distillate and Heavy Streams

| Light Distillate Properties (250-500° F.) | |
|---|---|
| Flash point, ° F. | 111 |
| Freeze point, ° F. | <−76 |
| Cloud point, ° F. | <−76 |
| Cetane Index | 48.2 |
| Specific Gravity | 0.7622 |
| Heavy Distillate Properties (500-700° F.) | |
| Flash point, ° F. | 273 |
| Freeze point, ° F. | <−76 |
| Cloud point, ° F. | <−76 |
| Cetane Index | 56.8 |
| Specific Gravity | 0.8084 |

TABLE 6-continued

Product Properties of Distillate and Heavy Streams

| Heavy Portion (700+ ° F.) | |
|---|---|
| Pour point, ° F. | −5.8 |
| Cloud point, ° F. | <−76 |
| Viscosity @ 40° C., cSt | 558.0 |
| Viscosity @ 100° C., cSt | 24.8 |

The product property data indicated that the process made very high quality distillate with excellent freeze and cloud points. The product provided by the processes herein could be used to improve the characteristics of kerosene, jet, or diesel blends. Additionally, the distillate fractions showed very good cetane index and low sulfur. The heavy portion showed excellent pour point and cloud point properties indicating this stream could be used to improve the characteristics of lubricant base oil.

The above products contained a small amount of olefins and they could be blended as they were with oxidation inhibitor(s) or sent to a hydrogenation unit to saturate the olefins before blending them into the various hydrocarbon products in an oil refinery.

While the invention has been described with respect to a limited number of embodiments, the specific features of one embodiment should not be attributed to other embodiments of the invention. No single embodiment is representative of all aspects of the invention. In some embodiments, the methods may include numerous steps not mentioned herein. In other embodiments, the methods do not include, or are substantially free of, steps not enumerated herein. Variations and modifications from the described embodiments exist. One or more steps may be omitted or combined but still achieve substantially the same results. The appended claims intend to cover all such variations and modifications as falling within the scope of the invention.

All publications and patent applications mentioned in this specification are herein incorporated by reference to the same extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A hydrocarbon product having less than 2 mole % olefinic hydrogens by $^1$H NMR, less than 0.1 mole % aromatic hydrogens by $^1$H NMR, an average carbon number from 15 to 40, a branching index from 45 to 70%, and wherein greater than 40 wt % of the hydrocarbon product has a boiling point distribution from 250° F. to 700° F.

2. The hydrocarbon product of claim 1 having 0.1-1.5 mole % olefinic hydrogens by $^1$H NMR.

3. The hydrocarbon product of claim 1 having from 45 wt % to 90 wt % product boiling from 250° F. to 700° F.

4. The hydrocarbon product of claim 1 having an average carbon number from 15 to 35.

5. The hydrocarbon product of claim 1 having an average carbon number from 21 to 34.

6. The hydrocarbon product of claim 1 having a branching index from 50 to 63%.

* * * * *